US012109089B2

(12) United States Patent
Kuo et al.

(10) Patent No.: US 12,109,089 B2
(45) Date of Patent: *Oct. 8, 2024

(54) INDIVIDUALIZED ORTHODONTIC TREATMENT INDEX

(71) Applicant: Align Technology, Inc., San Jose, CA (US)

(72) Inventors: Eric E. Kuo, San Jose, CA (US); Vadim Matov, San Jose, CA (US); Larry Lai, San Jose, CA (US); Fuming Wu, Pleasanton, CA (US); Jihua Cheng, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/168,558

(22) Filed: Feb. 13, 2023

(65) Prior Publication Data

US 2023/0293265 A1 Sep. 21, 2023

Related U.S. Application Data

(63) Continuation of application No. 14/967,598, filed on Dec. 14, 2015, now Pat. No. 11,612,454, which is a
(Continued)

(51) Int. Cl.
*A61C 7/00* (2006.01)
*A61B 5/00* (2006.01)
(Continued)

(52) U.S. Cl.
CPC ............ *A61C 7/002* (2013.01); *A61B 5/1128* (2013.01); *A61B 5/7246* (2013.01); *A61C 7/00* (2013.01);
(Continued)

(58) Field of Classification Search
None
See application file for complete search history.

(56) References Cited

U.S. PATENT DOCUMENTS 5,368,478 A * 11/1994 Andreiko ................. A61C 7/00
433/24
5,879,158 A * 3/1999 Doyle ................... A61C 9/0053
433/24
(Continued)

*Primary Examiner* — Akash Saxena
(74) *Attorney, Agent, or Firm* — Shay Glenn LLP

(57) ABSTRACT

Systems, methods, and non-transitory computing device readable media for determining an individualized orthodontic treatment index. One embodiment includes generating a target dental model by modifying an initial dental model, graphically marking dental references on the target dental model including assigning contact points between adjacent first and second teeth of the target dental model, generating a treatment outcome dental model representing the patient's dentition after at least a portion of the orthodontic treatment has been completed, mapping the dental references marked on the target dental model to the treatment outcome dental model, and calculating an individualized treatment index score for the treatment outcome dental model according to one or more differences between the target dental model and the treatment outcome dental model.

20 Claims, 6 Drawing Sheets

Related U.S. Application Data continuation of application No. 12/771,472, filed on Apr. 30, 2010, now Pat. No. 9,211,166.

(51) Int. Cl.
- *A61B 5/11* (2006.01)
- *G06F 3/041* (2006.01)
- *G06F 30/20* (2020.01)
- *G16C 20/70* (2019.01)
- *G16H 50/50* (2018.01)
- *G16H 20/40* (2018.01)
- *G16H 30/40* (2018.01)

(52) U.S. Cl.
CPC .............. *G06F 3/041* (2013.01); *G06F 30/20* (2020.01); *G16C 20/70* (2019.02); *G16H 50/50* (2018.01); *G06T 2210/12* (2013.01); *G16H 20/40* (2018.01); *G16H 30/40* (2018.01)

(56) References Cited

U.S. PATENT DOCUMENTS

| | | | |
|---|---|---|---|
| 6,227,851 B1 | 5/2001 | Chishti et al. | |
| 6,299,440 B1 | 10/2001 | Phan et al. | |
| 6,318,994 B1 | 11/2001 | Chishti et al. | |
| 6,371,761 B1 | 4/2002 | Cheang et al. | |
| 6,457,972 B1* | 10/2002 | Chishti | G06F 30/20 |
| | | | 433/24 |
| 6,488,499 B1 | 12/2002 | Miller | |
| 6,554,611 B2 | 4/2003 | Chishti et al. | |
| 6,582,229 B1 | 6/2003 | Miller et al. | |
| 6,688,886 B2 | 2/2004 | Hughes et al. | |
| 6,726,478 B1 | 4/2004 | Isiderio et al. | |
| 7,063,532 B1 | 6/2006 | Jones et al. | |
| 7,074,038 B1 | 7/2006 | Miller | |
| 7,077,647 B2* | 7/2006 | Choi | A61C 7/00 |
| | | | 433/213 |
| 7,108,508 B2 | 9/2006 | Hedge et al. | |
| 7,156,661 B2* | 1/2007 | Choi | A61C 7/002 |
| | | | 433/213 |
| 7,160,107 B2 | 1/2007 | Kopelman et al. | |
| 7,293,988 B2 | 11/2007 | Wen | |
| 7,309,230 B2 | 12/2007 | Wen | |
| 7,357,634 B2 | 4/2008 | Knopp | |
| 7,555,403 B2 | 6/2009 | Kopelman et al. | |
| 7,736,147 B2 | 6/2010 | Kaza et al. | |
| 7,844,356 B2 | 11/2010 | Matov et al. | |
| 7,878,804 B2 | 2/2011 | Korytov et al. | |
| 7,942,672 B2 | 5/2011 | Kuo | |
| 7,970,627 B2* | 6/2011 | Kuo | A61C 7/00 |
| | | | 705/2 |
| 8,044,954 B2 | 10/2011 | Kitching et al. | |
| 8,260,591 B2 | 9/2012 | Kass et al. | |
| 8,562,338 B2 | 10/2013 | Kitching et al. | |
| 8,591,225 B2 | 11/2013 | Wu et al. | |
| 8,788,285 B2 | 7/2014 | Kuo | |
| 8,930,219 B2 | 1/2015 | Trosien et al. | |
| 9,037,439 B2 | 5/2015 | Kuo et al. | |
| 9,060,829 B2 | 6/2015 | Sterental et al. | |
| 9,125,709 B2 | 9/2015 | Matty | |
| 9,144,472 B2* | 9/2015 | Isaacson | A61C 7/002 |
| 9,364,296 B2 | 6/2016 | Kuo | |
| 9,375,300 B2 | 6/2016 | Matov et al. | |
| 10,463,452 B2 | 11/2019 | Matov et al. | |
| 10,617,489 B2 | 4/2020 | Grove et al. | |
| 10,722,328 B2 | 7/2020 | Velazquez et al. | |
| 10,758,322 B2* | 9/2020 | Pokotilov | A61C 7/002 |
| 10,792,127 B2 | 10/2020 | Kopelman et al. | |
| 10,828,130 B2 | 11/2020 | Pokotilov et al. | |
| 10,835,349 B2 | 11/2020 | Cramer et al. | |
| 10,952,817 B1* | 3/2021 | Raslambekov | G06T 19/00 |
| 10,973,611 B2 | 4/2021 | Pokotilov et al. | |
| 10,993,782 B1* | 5/2021 | Raslambekov | G06T 19/00 |
| 10,996,813 B2 | 5/2021 | Makarenkova et al. | |
| 10,997,727 B2 | 5/2021 | Xue et al. | |
| 11,020,205 B2 | 6/2021 | Li et al. | |
| 11,020,206 B2 | 6/2021 | Shi et al. | |
| 11,026,766 B2 | 6/2021 | Chekh et al. | |
| 11,033,359 B2 | 6/2021 | Velazquez et al. | |
| 11,071,608 B2 | 7/2021 | Derakhshan et al. | |
| 11,109,945 B2* | 9/2021 | Salah | A61C 9/0053 |
| 11,151,753 B2 | 10/2021 | Gao et al. | |
| 11,154,381 B2 | 10/2021 | Roschin et al. | |
| 11,259,896 B2 | 3/2022 | Matov et al. | |
| 11,278,377 B1* | 3/2022 | Raslambekov | G06T 17/20 |
| 11,357,598 B2 | 6/2022 | Cramer | |
| 11,395,717 B2 | 7/2022 | Yuryev et al. | |
| 11,432,908 B2 | 9/2022 | Kopelman et al. | |
| 11,464,604 B2 | 10/2022 | Makarenkova et al. | |
| 11,478,334 B2 | 10/2022 | Matov et al. | |
| 11,484,389 B2 | 11/2022 | Sterental et al. | |
| 11,521,732 B2 | 12/2022 | Levin et al. | |
| 11,534,272 B2 | 12/2022 | Li et al. | |
| 11,553,988 B2 | 1/2023 | Mednikov et al. | |
| 11,642,195 B2 | 5/2023 | Gao et al. | |
| 11,651,494 B2 | 5/2023 | Brown et al. | |
| 11,654,001 B2 | 5/2023 | Roschin et al. | |
| 2001/0038705 A1* | 11/2001 | Rubbert | A61C 7/00 |
| | | | 382/128 |
| 2002/0010568 A1* | 1/2002 | Rubbert | A61C 7/146 |
| | | | 703/6 |
| 2002/0042038 A1* | 4/2002 | Miller | A61C 7/00 |
| | | | 433/215 |
| 2002/0072027 A1* | 6/2002 | Chishti | A61C 7/00 |
| | | | 433/24 |
| 2002/0156652 A1* | 10/2002 | Sachdeva | A61C 7/146 |
| | | | 705/2 |
| 2003/0129565 A1* | 7/2003 | Kaza | A61C 11/00 |
| | | | 433/213 |
| 2003/0143509 A1 | 7/2003 | Kopelman et al. | |
| 2003/0207227 A1 | 11/2003 | Abolfathi | |
| 2004/0137400 A1 | 7/2004 | Chishti et al. | |
| 2005/0019721 A1* | 1/2005 | Chishti | A61C 7/00 |
| | | | 433/24 |
| 2005/0182654 A1 | 8/2005 | Abolfathi et al. | |
| 2005/0186526 A1* | 8/2005 | Stewart | A61C 7/00 |
| | | | 433/24 |
| 2005/0271996 A1* | 12/2005 | Sporbert | A61C 7/00 |
| | | | 433/24 |
| 2006/0127836 A1 | 6/2006 | Wen | |
| 2006/0127852 A1 | 6/2006 | Wen | |
| 2006/0127854 A1 | 6/2006 | Wen | |
| 2007/0003907 A1* | 1/2007 | Chishti | A61C 7/00 |
| | | | 702/19 |
| 2007/0081951 A1* | 4/2007 | Stookey | A61K 8/4926 |
| | | | 424/49 |
| 2007/0141525 A1* | 6/2007 | Cinader, Jr. | A61C 7/146 |
| | | | 433/23 |
| 2007/0184411 A1* | 8/2007 | Stapleton | A61C 19/04 |
| | | | 433/215 |
| 2008/0020350 A1* | 1/2008 | Matov | G06T 17/20 |
| | | | 433/213 |
| 2008/0076086 A1* | 3/2008 | Kitching | A61C 7/00 |
| | | | 433/68 |
| 2008/0113317 A1* | 5/2008 | Kemp | G06T 7/0012 |
| | | | 382/164 |
| 2008/0182220 A1* | 7/2008 | Chishti | A61C 7/002 |
| | | | 433/24 |
| 2008/0248443 A1* | 10/2008 | Chishti | G06T 17/00 |
| | | | 433/24 |
| 2008/0305451 A1* | 12/2008 | Kitching | A61C 7/00 |
| | | | 433/24 |
| 2008/0305454 A1* | 12/2008 | Kitching | A61C 7/00 |
| | | | 433/24 |
| 2009/0034811 A1* | 2/2009 | Kuo | A61C 7/00 |
| | | | 382/128 |
| 2009/0148809 A1* | 6/2009 | Kuo | G06F 30/00 |
| | | | 433/24 |
| 2009/0191503 A1* | 7/2009 | Matov | A61C 7/16 |
| | | | 433/2 |

(56) References Cited

U.S. PATENT DOCUMENTS

| | | | |
|---|---|---|---|
| 2009/0316966 A1* | 12/2009 | Marshall | G06T 19/00 382/128 |
| 2010/0009308 A1 | 1/2010 | Wen et al. | |
| 2010/0068672 A1 | 3/2010 | Arjomand et al. | |
| 2010/0092907 A1 | 4/2010 | Knopp | |
| 2010/0167243 A1 | 7/2010 | Spiridonov et al. | |
| 2010/0179789 A1* | 7/2010 | Sachdeva | A61C 9/0046 703/11 |
| 2011/0104630 A1* | 5/2011 | Matov | A61C 7/00 703/1 |
| 2011/0269097 A1* | 11/2011 | Sporbert | A61C 7/00 433/24 |
| 2011/0270588 A1* | 11/2011 | Kuo | A61B 5/1128 703/2 |
| 2013/0204599 A1 | 8/2013 | Matov et al. | |
| 2014/0200863 A1* | 7/2014 | Kamat | G06T 19/00 703/1 |
| 2015/0269776 A1* | 9/2015 | Jesenko | G06T 17/10 345/420 |
| 2016/0095668 A1* | 4/2016 | Kuo | G06F 30/20 703/6 |
| 2016/0310235 A1 | 10/2016 | Derakhshan et al. | |
| 2017/0128161 A1* | 5/2017 | See | G06T 19/00 |
| 2017/0273760 A1 | 9/2017 | Morton et al. | |
| 2018/0344430 A1* | 12/2018 | Salah | A61C 7/12 |
| 2019/0328487 A1 | 10/2019 | Levin et al. | |
| 2019/0328488 A1 | 10/2019 | Levin et al. | |
| 2020/0155274 A1 | 5/2020 | Pimenov et al. | |
| 2020/0297458 A1 | 9/2020 | Roschin et al. | |
| 2020/0306011 A1 | 10/2020 | Chekhonin et al. | |
| 2020/0306012 A1 | 10/2020 | Roschin et al. | |
| 2021/0045843 A1* | 2/2021 | Pokotilov | A61C 7/002 |
| 2021/0134436 A1 | 5/2021 | Meyer et al. | |
| 2021/0174477 A1 | 6/2021 | Shi et al. | |
| 2023/0293265 A1* | 9/2023 | Kuo | A61C 7/002 703/6 |

* cited by examiner

INDIVIDUALIZED ORTHODONTIC TREATMENT INDEX

CLAIM OF PRIORITY

The present application is a continuation of U.S. patent application Ser. No. 14/967,598, filed Dec. 14, 2015, now U.S. Pat. No. 11,612,454, which is a continuation of U.S. patent application Ser. No. 12/771,472, filed Apr. 30, 2010, now U.S. Pat. No. 9,211,166, the disclosures of each are incorporated in their entirety herein by reference.

BACKGROUND

The present disclosure is related generally to the field of orthodontics. More particularly, the present disclosure is related to using an individualized orthodontic treatment index.

Some objectives in the field of orthodontics are to realign a patient's teeth to positions where the teeth function well and align the teeth to provide a pleasing aesthetic appearance. One goal of an orthodontic treatment professional is to take the patient's dentition from a starting arrangement to a final arrangement.

Further, when using fixed brackets and wires (i.e., braces) may be applied to a patient's teeth to gradually reposition them from an initial arrangement to a final arrangement. The diagnosis and treatment planning process of orthodontic cases may be imprecise as the final dentition of a patient may be based on the knowledge and expertise of the treatment professional in assembling various parameters in an assessment of each patient's condition and in a determination of a final position for each tooth. Different treatment professionals may vary in their definitions of individual orthodontic parameters and their definition of how a case should ideally be treated may also vary.

To overcome some of these subjective issues, various indices have been used to more objectively define a patient's dentition, including initial dentition, progress dentition, and final outcome dentition. For example, the PAR (Peer Assessment Rating) index identifies how far a dentition is from a good occlusion. A score is assigned to various occlusal traits which make up a malocclusion. The individual scores are summed to obtain an overall total, representing the degree a case deviates from ideal functional alignment and occlusion. The PAR score is then calibrated to a known standard set of orthodontic conditions so this individual is able to rate new cases similarly. The PAR score may be weighted or unweighted, depending on the relative importance of certain components of the occlusion.

In PAR, a score of zero would indicate ideal alignment and positioning of all orthodontic dental components, as defined by generally accepted occlusal and aesthetic relationships the orthodontic community has adopted. Higher scores would indicate increased levels of irregularity. The PAR score can be recorded on pre-, mid- and/or post-treatment dental casts. The difference between any two of these scores represents the degree of improvement as a result of orthodontic intervention during the represented portion of treatment. The score may be represented as an absolute point improvement or as a percentage improvement with respect to an earlier treatment point used for the comparison.

In addition to the PAR index, other indices may be used such as Index of Complexity Outcome and Need (ICON), Index of Orthodontic Treatment Need (IOTN) and American Board of Orthodontics (ABO) indices. These indices also rely on individual dental measurements in order to derive an assessment of deviation from an ideal. One drawback to using such indices is that the individual dental measurements may be based on landmarks that are identified on the patient's dentition by a treatment professional. After identifying landmarks at an earlier stage of treatment, the treatment professional may not be able to accurately identify the same landmarks at a later stage of treatment because the patient's dentition may have changed during the course of treatment.

DETAILED DESCRIPTION

Figure 1A:
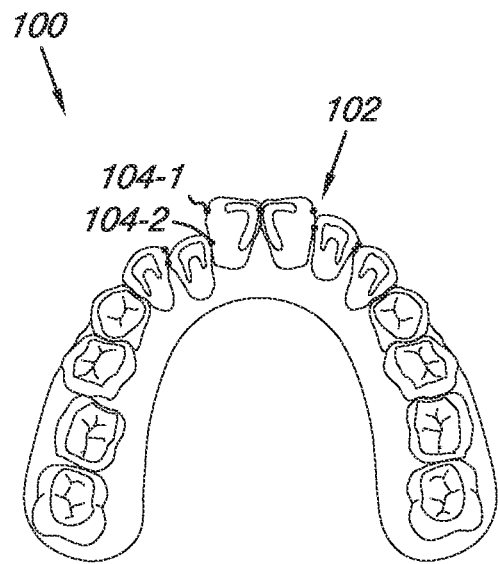
FIG. 1A illustrates an initial virtual dental model having dental references assigned thereto according to a prior art method.

Embodiments of the present disclosure include computing device related, system, and method embodiments for using an individualized orthodontic treatment index. For example, one or more embodiments include, a computing device implemented method that includes receiving an initial virtual dental model from a first scan of a patient's dentition, modifying the initial virtual dental model to create a target virtual dental model according to a treatment goal, and assigning a number of dental references to the target virtual dental model.

The first scan of the patient's dentition can be a scan performed prior to treatment initiation or before the completion of treatment. Assigning dental references to the target virtual dental model can be beneficial as compared to assigning target dental references to the initial virtual dental model (e.g., assigning dental references to the initial model in positions where the treatment professional believes they should be) because the correct location of certain landmarks such as contact points and cusp tips (which may have some degree of uncertainty in identifying when using the initial state) may be more accurate when using the context of the desired final outcome to assist in the identification process.

Some embodiments can include receiving a treatment outcome virtual dental model from a second scan of the patient's dentition and mapping the number of dental references from the target virtual dental model to the treatment outcome virtual dental model. The second scan of the patient's dentition can be a scan performed after treatment has been completed or after some portion of treatment has been completed. Mapping landmarks established on the treatment target virtual dental model to the treatment outcome virtual dental model can provide for a more accurate assessment and comparison between the actual treatment outcome achieved and the target treatment outcome for the patient because the same reference points are being used to derive measurements in both the initial and outcome models. Mapping can help reduce errors associated with misidentification of landmarks between different models.

Embodiments can include calculating an initial deviation from ideal using a target-normalized setup as an "ideal." As opposed to some previous approaches, the individualized treatment index score can be relevant to all types of cases and not just permanent non-worn, ideally shaped patient dentition. For example, an occlusion score can be established for restored, primary, and/or worn dentition without these conditions negatively contributing to the score. By having broader applicability, the individualized treatment index score can establish baselines of quality for a wider array of treatment applications.

Embodiments can include calculating an individualized treatment index score for the actual treatment outcome through a virtual dental model of the outcome according to one or more differences between the target virtual dental model and the treatment outcome virtual dental model based on the number of mapped dental references. This can improve the accuracy of measurements by reducing the error introduced from landmark identification on models representing multiple points in treatment when such models are evaluated individually.

Treatment professionals typically establish their target as the ideal treatment outcome based upon one or more of these scoring systems and discontinue treatment when they are as close as they can possibly get to the ideal treatment outcome. However, with the use of 3-D computer graphics software services and programs, the treatment professional can establish a custom treatment target specific to each individual patient, and this target may be a limited treatment target and not ideal in every component. In part, this may be due to unwillingness by the patient to undergo certain aspects of treatment in order to achieve an ideal outcome (e.g., jaw surgery, headgear, elective restorative dental care, etc.).

Thus, if the treatment professional is able to achieve 100% of the intended limited target, the treatment may still be deemed a success, even though the target might only represent a 75% improvement relative to an ideal target. Without characterizing the degree of improvement relative to the intended target, a treatment might be mistakenly categorized as being unsuccessful when it was highly successful in the eyes of both the treatment professional and the patient. According to the present disclosure, a context of the intended individual treatment goal can determine the degree of treatment success achieved, rather than an absolute index.

Some clinical measurements are benchmarked against standards using relationships between specific dental landmarks. A degree of error can be introduced into scoring a dental model and/or calculating an index score based on the selection of a specific reference (e.g., landmark) and/or based on the repeatability of the selection between different models (e.g., representing different points in treatment). The accuracy to which the landmark is selected and/or repeated by the user can determine whether or not the measurement represents the correct relationship found in the model.

A user may have difficulty in identifying a specific dental landmark due to the shape of the patient's anatomy. For example, proper identification of a cusp tip may be hindered by the tooth having been worn down. Furthermore, the "same" reference point may be inadvertently selected at different locations on different dental models that represent different treatment points for the patient.

Virtual dental models from a scan of a patient's dentition can be provided with computer-aided tooth treatment systems. An initial digital data set (IDDS) representing an initial tooth arrangement may be obtained. The IDDS may be obtained in a variety of ways. For example, the patient's teeth may be imaged to obtain digital data using direct or indirect structured light, X-rays, three-dimensional X-rays, computer-aided tomographic images or data sets, magnetic resonance images, photographic reconstruction, and/or other imaging techniques.

A cast (e.g., a plaster cast and/or mold) of the patient's teeth may be scanned using an x-ray, laser scanner, destructive scanner, structured light, or other range acquisition system to produce the IDDS. The data set produced by the range acquisition system may be converted to other formats to be compatible with the software which is used for manipulating images within the data set, as described herein.

The data set can be used to create a series of orthodontic aligners used to move teeth though successive arrangements from molds of the patient's teeth or digital models of the patient's teeth. One example of such a system is described in more detail in U.S. Pat. No. 5,975,893 to Chisti et al., which is assigned to Align Technology, Inc.

Although the overarching term "orthodontics" is used herein, the present disclosure may relate to treatments of an orthognathic nature. For example, in cases including treatment of a patient's underlying skeletal structure, teeth may be rearranged by surgically repositioning underlying bones that hold the teeth in order to achieve a desired final bite arrangement. In both orthodontic and orthognathic treatment approaches, alignment of the teeth may be evaluated pre-, mid-, and/or post-treatment.

Referring now to FIG. 1A, there is illustrated an initial virtual dental model having dental references assigned thereto according to a prior art method. The prior art method includes identifying the dental references 102 (e.g., contact points 104-1 and 104-2 between various teeth as illustrated in FIG. 1A). The treatment professional can use his/her best judgment to identify and assign the dental references 102 to the initial virtual dental model 100.

After the dental references 102 have been assigned to the initial virtual dental model 100, a score can be calculated according to a prior art method such as PAR, ICON, IOTN, and ABO, as described herein. For example, a score can be calculated based on a measurement of the distance between contact points 104-1 and 104-2, where an "ideal" case would have substantially zero distance between contact points 104-1 and 104-2 for various teeth. Scores for cases varying from the ideal can have a higher value.

For the various prior art methods, the ideal case is a pre-defined orthodontic norm with assumptions about the phase, shape, and condition of the teeth. Again, scoring based on such an ideal case assumes that the ideal can actually be achieved. Thus, for example, the score of the initial virtual dental model 100 illustrated in FIG. 1A is "5," relative to an ideal case having a score of "0."

Figure 1B:
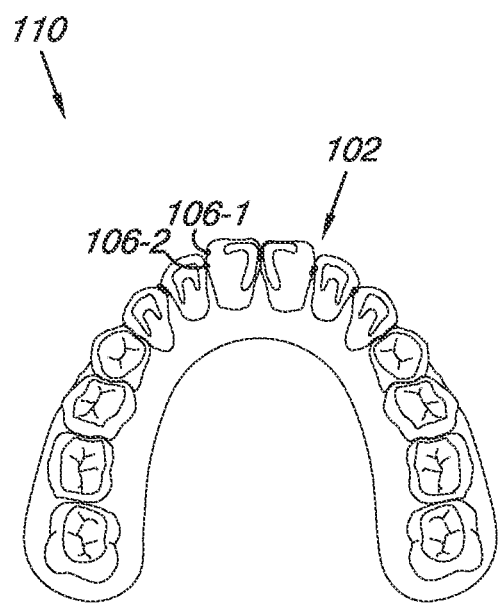
FIG. 1B illustrates a treatment outcome virtual dental model corresponding to the initial virtual dental model illustrated in FIG. 1A having dental references assigned thereto according to a prior art method.

FIG. 1B illustrates a treatment outcome virtual dental model corresponding to the initial virtual dental model illustrated in FIG. 1A having dental references assigned thereto according to a prior art method. The treatment professional can use his best judgment to assign the dental references 102 to the treatment outcome virtual dental model 110 with reference to the dental references 102 assigned to the initial virtual dental model 100. That is, for each dental reference 102 assigned to the initial virtual dental model 100, the treatment professional can attempt to assign a dental reference 102 to the treatment outcome virtual dental model 110 at the same point or points.

For example, the treatment professional can attempt to assign contact points 106-1 and 106-2 to the treatment outcome virtual dental model 110 at the exact same locations on the respective teeth as the contact points 104-1 and 104-2 assigned to the initial virtual dental model 100. However, as the reader will appreciate, there will be some noise in the data corresponding to the assigned points due to inaccuracy in the assignment. The scorer may choose a location in the outcome model corresponding to a similar point identified in the initial model, which may not necessarily be the exact same location for that point as that identified in the initial model.

The accuracy of such prior art methods relies on the treatment professional's ability to pick the exact same points among various virtual dental models and to pick the "correct points," (e.g., contact points 106-1 and 106-2) assuming such points exist. Furthermore, the score is based on a pre-determined absolute scale to which the initial 100 and treatment outcome 110 virtual dental models are compared. As described herein, in many cases the "ideal" cannot be achieved, such as in some cases of primary dentition, mixed dentition, worn dentition, pre-restoration, extensive restoration, limited treatment, lower incisor extraction, tooth-size discrepancy, and the like.

Thus, for example, the score of the treatment outcome virtual dental model 110 illustrated in FIG. 1B can be 1.6. As compared to the score of the initial virtual dental model 100 illustrated in FIG. 1A, a 68% improvement has been achieved according to this scoring system. That is, 5−1.6=3.4, where 5 represents a score of the initial virtual dental model 100 and 1.6 represents the score of the treatment outcome virtual dental model 110. 3.4÷5=0.68, where 0.68 represents the fraction of improvement achieved toward an ideal condition. Thus, the 68% improvement may seem to indicate a rather poor treatment outcome. However, the score provided by such prior art methods is relative to a notion of an "ideal," and does not take into account whether that "ideal" can be realistically achieved.

Additional complications of some prior art approaches include dental references that are broad surface areas rather than singular points. The potential for multiple singular points to exist within a broad surface area for such types of dental references may lead to variability in the determination of the reference, particularly among different virtual dental models (e.g., at different stages of treatment).

Furthermore, such prior art scoring systems can yield variability issues between different treatment professionals who may apply the scoring systems differently and/or assign dental references differently, etc. For example, consider two hypothetical patients having the exact same dental conditions and who are treated by two different professionals and achieve the exact same physical treatment outcome. Based on the abilities of the two treatment professionals to use the prior art scoring systems, different treatment index scores may result although the actual physical outcome of treatment was exactly the same for both patients. This is known as inter-operator variability. While calibration between operators can reduce the variability, it is generally not eliminated.

Figure 2A:
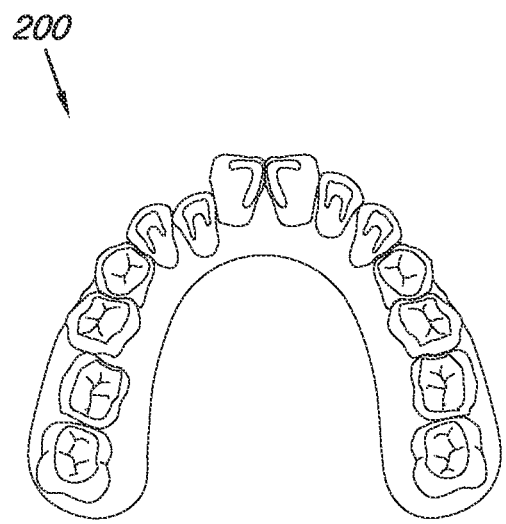
FIG. 2A illustrates an initial virtual dental model according to one or more embodiments of the present disclosure.

FIG. 2A illustrates an initial virtual dental model according to one or more embodiments of the present disclosure. As described herein, the initial virtual dental model 200 can be obtained from a first scan of a patient's dentition prior to treatment or at an intermediate state of treatment (e.g., before treatment has been completed). Rather than assigning dental references to the initial virtual dental model 200, one or more embodiments of the present disclosure first define a specific treatment goal and use a target virtual dental model based on that treatment goal.

Figure 2B:
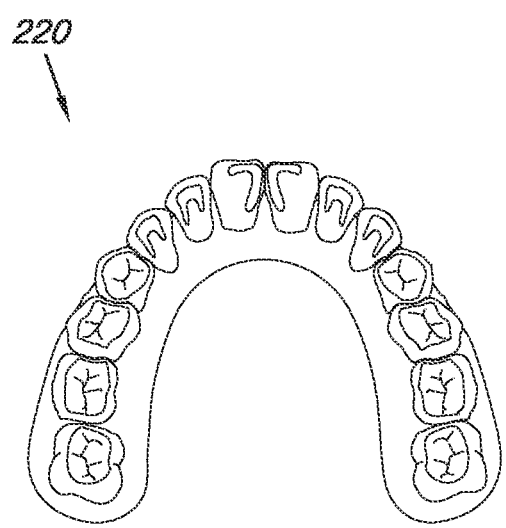
FIG. 2B illustrates a target virtual dental model corresponding to the initial virtual dental model illustrated in FIG. 2A according to the present disclosure.

FIG. 2B illustrates a target virtual dental model corresponding to the initial virtual dental model illustrated in FIG. 2A according to the present disclosure. The target virtual dental model 220 can be created by modifying the initial virtual dental model 200 according to one or more treatment goals. One example of creating a target virtual dental model is described in U.S. Pat. No. 7,134,874 to Chisti et al., which is assigned to Align Technology, Inc.

The one or more treatment goals are case-specific (e.g., specific to the particular patient on which the initial virtual dental 200 model was based). Because the one or more treatment goals are case-specific, the target virtual dental model 220 can apply to cases that could not be accurately scored by prior art treatment indices such as mixed dentition, primary dentition, restored/worn dentition, missing teeth dentition, tooth-size discrepancy dentition, pre-restorative dentition, and the like.

Thus, the target virtual dental model 220 illustrated in FIG. 2B represents a modification of the initial virtual dental model 200 illustrated in FIG. 2A according to one or more treatment goals defined by a treatment professional associated with the patient. The target virtual dental model 220 does not have to correspond to an "ideal" treatment outcome as described herein (e.g., a generic ideal dentition that does correspond to any particular patient). The target virtual dental model 220 represents the treatment professional's opinion as to the best outcome for the particular patient that can reasonably be achieved with the orthodontic treatment methods available to the treatment professional. That is, a standard against which to measure the "quality" of the actual treatment outcome for the particular patient has been defined in advance by the treatment professional with the target virtual dental model 220.

Figure 2C:
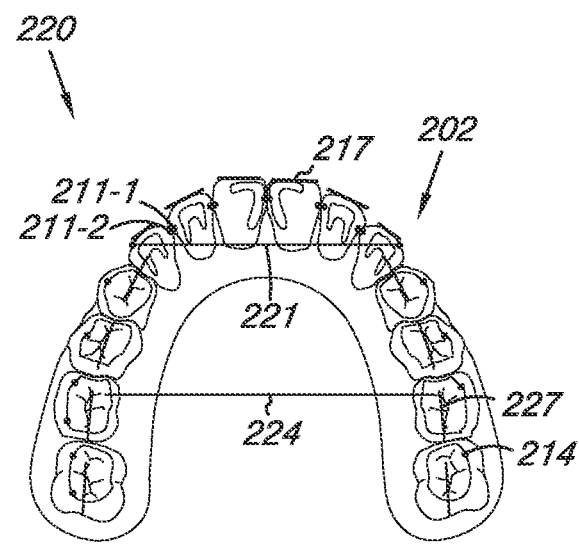
FIG. 2C illustrates the target virtual dental model illustrated in FIG. 2B having dental references assigned thereto according to one or more embodiments of the present disclosure.

FIG. 2C illustrates the target virtual dental model illustrated in FIG. 2B having dental references assigned thereto according to one or more embodiments of the present disclosure. In contrast to some prior art methods, dental references 202 in the embodiment illustrated in FIG. 2A-2D are first assigned to a target virtual dental model 220 (e.g., instead of to the existing condition).

One of ordinary skill in the art will appreciate the various dental references that can be assigned, such as, contact points 211-1 and 211-2 between teeth, cusp tips 214, facial lines 217, cuspid width 221, and molar width 224, among others. Contact points such as contact points 211-1 and 211-2 can be used for determination of alignment, cusp tip points 214 can be used for determination of arch length, cuspid width 221 and molar width 224 can be used for a determination of arch width, facial lines 217 can be used for determination of arch curve, and facial aspect of clinical crown (FACC) lines (not shown) can be used for determination of angulation and inclination. FACC can be a subset of facial lines. Any line on the facial surface of the tooth could be considered to be a facial line (e.g., including horizontal references).

According to the present disclosure, the dental references 202 are assigned to the target virtual dental model 220 based on the treatment professional's judgment of a specific target outcome, as opposed to the dental references 202 being assigned to "idealized" locations based on a generic "ideal" case that may be unachievable. Such embodiments, allow the treatment professional to pinpoint a more accurate, if not exact, location for the dental references 202 on the target virtual dental model.

The location of the dental references 202 assigned to the target virtual dental model 220 by the treatment professional can be assigned in an algorithmically determined fashion. Dental references 202 can be used to define "good" alignment for a treatment outcome (e.g., if corresponding dental references on the patient's treatment outcome virtual model 210 (e.g., as illustrated in FIG. 2E) match the dental references 202 on the target virtual dental model 220, then "good" alignment has been achieved). The dental references 202 on the target virtual dental model 220 can serve as references from which to measure differences in an initial virtual dental model 200 and/or a treatment outcome virtual dental model 210 (e.g., in order to evaluate the patient's initial condition and/or the progress/actual treatment outcome).

As such, a score can be calculated for the target virtual dental model 220. The score can be calculated using any of a number of available scoring systems such as those described herein, or some other scoring system. However, contrary to prior art methods, both the patient's initial condition and treatment outcome are scored against a defined target (e.g., treatment outcome goal) that is individualized to the patient, according to the context of the established target as determined by the treatment professional, as opposed to being scored against an idealized generic goal that may be an inappropriate basis of comparison for the particular patient being evaluated (e.g., using an adult dentition definition of "ideal" as a basis to score a child's dentition). For example, the target virtual dental model 220 can have a score of 1 (e.g., representing a less than "ideal" target outcome, as opposed to a score of 0 for an "ideal" outcome).

Figure 2D:
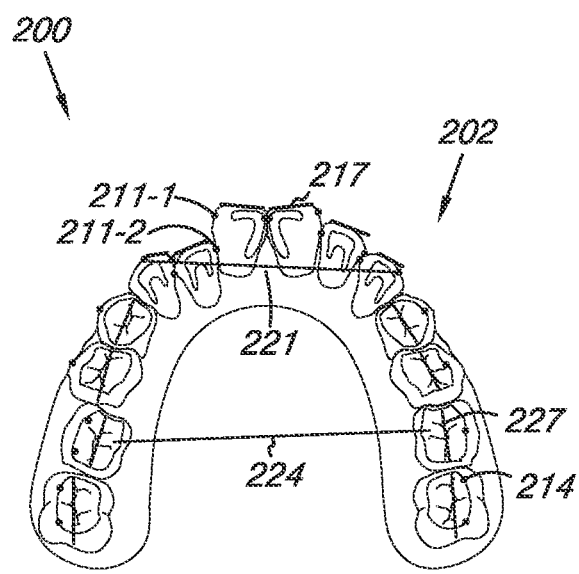
FIG. 2D illustrates the initial virtual dental model illustrated in FIG. 2A having the dental references assigned to the target virtual dental model illustrated in FIG. 2B mapped thereto according to one or more embodiments of the present disclosure.
Figure 2E:
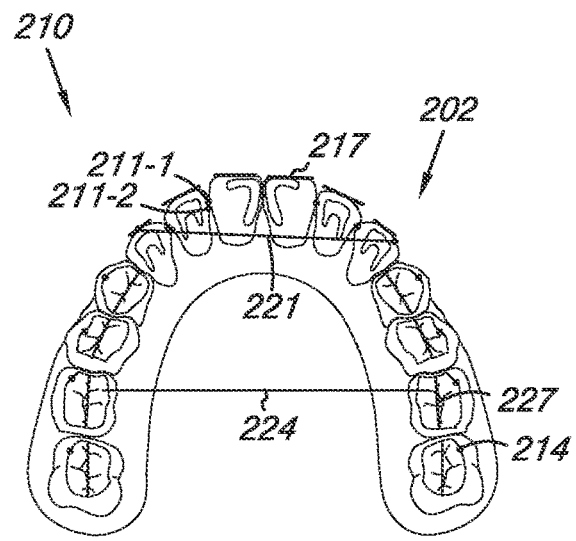
FIG. 2E illustrates a treatment outcome virtual dental model having the dental references assigned to the target virtual dental model illustrated in FIG. 2B mapped thereto according to one or more embodiments of the present disclosure.

FIG. 2D illustrates the initial virtual dental model illustrated in FIG. 2A having the dental references assigned to the target virtual dental model illustrated in FIG. 2B mapped thereto according to one or more embodiments of the present disclosure. The dental references 202 from the target virtual dental model 220 can be mapped to the initial virtual dental model 200. Because the dental references 202 can be mapped (e.g., by computing device implemented superimpositions of the dental references 202), the dental references 202 illustrated on the initial virtual dental model 200 represent the exact same references (e.g., points) on the virtual teeth, although the orientation (e.g., special positions) of the references may change with the changed orientation of the teeth relative to the target virtual dental model 220. The references can be in the same position on the respective teeth, but since the teeth may be in a different position due to the administered treatment, the position of a particular reference in space may be different.

The dental references 202 can be used to determine an amount of discrepancy between the initial virtual dental model 200 and the target virtual dental model 220. Similarly, a discrepancy between the outcome model 210 and an intermediate outcome model (not specifically illustrated) may also be calculated. A score can be calculated for the initial virtual dental model 200 and compared to the target virtual dental model 220 based at least in part on the special orientation differences between the dental references 202. As described above, the score can be calculated using any of a number of scoring systems. For example, the initial virtual dental model 200 can have a score of 6.

FIG. 2E illustrates a treatment outcome virtual dental model having the dental references assigned to the target virtual dental model illustrated in FIG. 2B mapped thereto according to one or more embodiments of the present disclosure. The treatment outcome virtual dental model 210 can be received from a second scan of the patient's dentition (e.g., a scan at the completion of treatment or at some point during treatment after the first scan). The dental references 202 can be mapped from the target virtual dental model 220 to the treatment outcome virtual dental model 210.

Assigning dental references 202 to the target virtual model 220 and then mapping the dental references 202 to the treatment outcome virtual model 210 can help reduce and/or eliminate inaccuracy (e.g., noise) associated with assignment of dental references to models corresponding to different points during treatment according to some prior art methods at least in part. Such inaccuracy can be reduced due, at least in part, to the accuracy of mapping algorithms as compared to dental reference transfers between various models performed manually by the treatment professional.

Mapping the dental references 202 from the target virtual dental model 220 to the initial virtual dental model 200 and/or the treatment outcome virtual dental model 210 can include the use of one or more algorithms including a transformation algorithm and/or a shrink-wrap algorithm. For example, a transformation algorithm can transform individual dental references 202 from a coordinate system associated with the target virtual dental model 220 to a coordinate system associated with the initial 200 and/or treatment outcome 210 virtual dental models. For example, a shrink-wrap algorithm can adjust coordinates of a particular dental reference in cases where the target virtual dental model 220 has a scale that differs from the initial 200 and/or treatment outcome 210 virtual dental models.

The dental references 202 can be used to determine an amount of discrepancy between the treatment outcome virtual dental model 210 and the target virtual dental model 220. A score can be calculated for the treatment outcome virtual dental model 210 and compared to the target virtual dental model 220 based at least in part on the discrepancies between corresponding dental references 202. As described above, the score can be calculated using any of a number of scoring systems. For example, the treatment outcome virtual dental model 210 can have a score of 1.3.

Using the scores calculated for the target virtual dental model 220 and the treatment outcome virtual dental model 210, a more meaningful evaluation of the treatment of the patient can be provided. Rather than comparing the patient's treatment outcome to the patient's initial condition within the context of a generic idealized outcome that might not be realistically attainable relative to the patient's initial condition, the patient's treatment outcome can be compared to the patient's initial condition within the context of a treatment goal specifically established by the treatment professional.

Thus, using the example scored given in the discussion above, a 94% improvement has been achieved according to this scoring system. That is, 6−1=5, where 6 represents a score of the patient's initial condition, 1 represents a score of the patient's target outcome condition, and 5 represents a score characterizing the total improvement that is determined to be the target appropriate for the patient. 6−1.3=4.7, where 1.3 represents a score of the patient's actual treatment outcome condition and 4.7 represents a score characterizing the total improvement actually achieved relative to the target goal. 4.7÷5=0.94, where 0.94 represents the fraction of possible improvement achieved based on the actual treatment outcome. This scoring can be contrasted with some previous approaches, which would assign a score of 0 to an ideal outcome and would rate this example case as only a 78% improvement (4.7÷6=0.78) despite a good outcome relative to the intended objective.

The individualized orthodontic treatment index scoring system described herein is advantageous over those previous approaches that relate outcome scores to the concept of an ideal goal rather than to a patient-specific, treatment professional defined goal because the scoring system yields a score that meaningfully characterizes treatment outcomes across all types of initial patient conditions. Prior art scoring systems can yield disproportionately positive results for patients having more "normal" initial conditions and disproportionately negative results for patients having more "abnormal" initial conditions. Such prior art systems can prevent patients who do not fit the norm from receiving an accurate assessment of their treatment outcomes, as their initial condition is inherently biased toward lower scores as a result of their disqualification from possibly achieving an ideal score.

Using the individualized orthodontic treatment index scoring system according to one or more embodiments of the present disclosure can allow for a more accurate assessment of "good" or "acceptable" scores and "bad" or "unacceptable" scores for many different types of initial patient conditions and not just for permanent non-restored adult teeth where no tooth-size discrepancy exists. Such scoring zones can be established for primary teeth, mixed dentition, significantly restored and/or occlusally worn teeth, pre-restorative set-ups, tooth-size discrepancy (even specific teeth of tooth-size discrepancy such as prior incisor extraction), limited treatment, and/or ideal conditions. Thus, the individualized orthodontic treatment index provides a contextually objective method of scoring orthodontic treatment.

An accumulation of retrospective data (e.g., in a database), such as the frequency of different types of initial patient conditions along with a corresponding treatment professional's preferred treatment objectives, would allow a correlation to be established between the individualized orthodontic treatment index and a predictability of a desired index outcome for future cases. Such correlation can be established as a predictability index.

Figure 3:
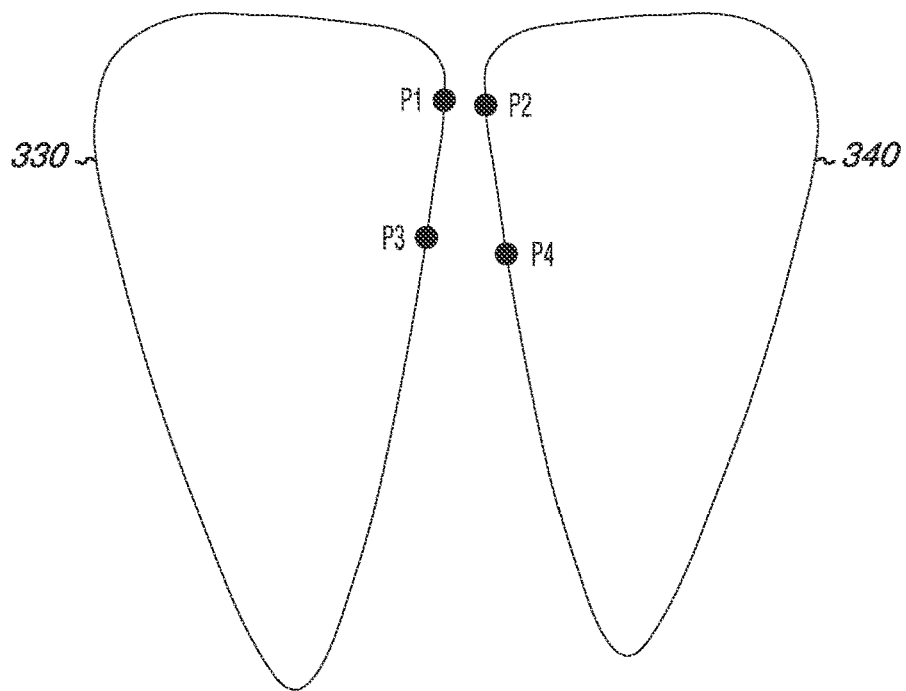
FIG. 3 illustrates an interproximation relationship between two spaced teeth according to one or more embodiments of the present disclosure.
Figure 4:
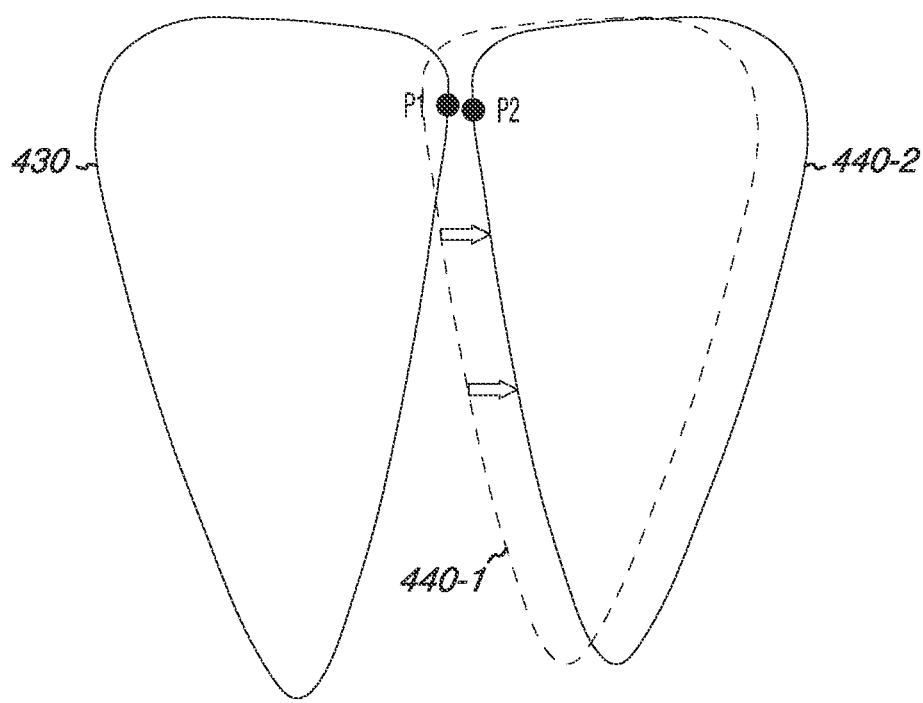
FIG. 4 illustrates an interproximation relationship between two overlapped teeth according to one or more embodiments of the present disclosure.
Figure 5:
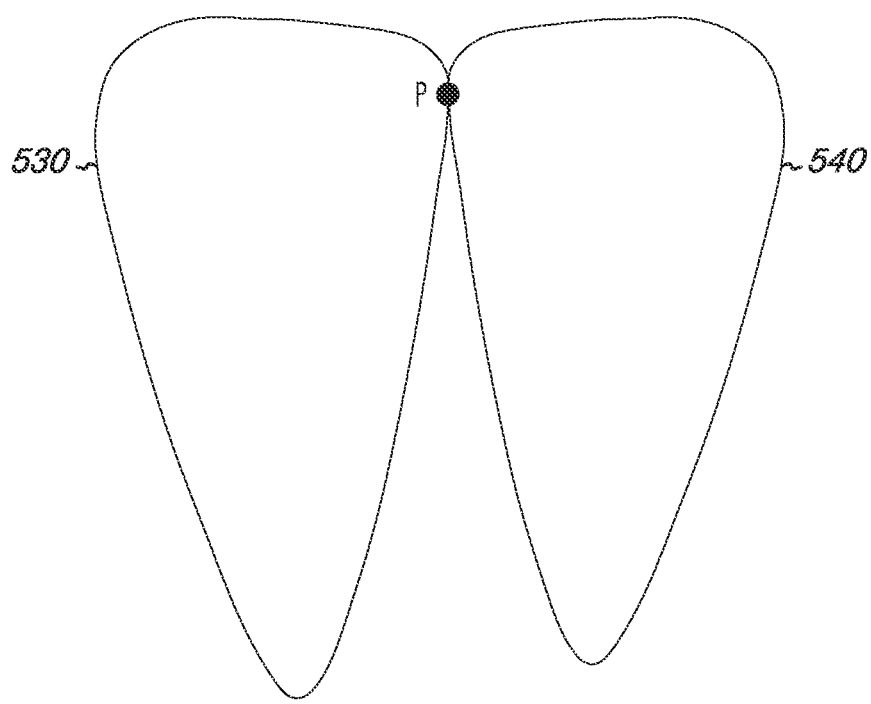
FIG. 5 illustrates an interproximation relationship between two point-contacted teeth according to one or more embodiments of the present disclosure.

As described herein, one example of a dental reference is a contact relationship between adjacent teeth based on a difference between contact points on individual teeth. FIGS. 3-5 illustrate different interproximation relationships between adjacent teeth. While an "ideal" treatment outcome may result in a point-contacted interproximation relationship (e.g., a single point of contact, P, as illustrated in FIG. 5) for all adjacent teeth, some patients may not have such a relationship as a realistic treatment goal for all of their adjacent tooth pairs.

For example, in a limited treatment, the goal may be to only treat the anterior teeth, without any treatment to the posterior teeth, which may contain one or more discrepancies in the contact relationships. Under a scoring system based on an ideal score, the impact of any achieved treatment outcome will be diluted to an extent by the discrepancies that exist in the areas not being treated. Accordingly, one or more embodiments of the present disclosure can assign dental references to a target virtual dental model having one or more virtual teeth that are not in an "ideal" configuration. According to one or more embodiments of the present disclosure, limited treatment cases can be evaluated to provide further insight as to whether a reported index is in line with the best practices of treatment professionals.

FIG. 3 illustrates an interproximation relationship between two spaced virtual teeth according to one or more embodiments of the present disclosure. A first tooth 330 and a second tooth 340 in a target virtual dental model may be spaced apart from one another. In such a scenario, a single contact point does not exist between the first tooth 330 and the second tooth 340. In cases where specific amounts of space are actually desirable as part of the treatment outcome (e.g., pre-restorative set-ups, set-ups where idiosyncratic familial characteristics are intended to be preserved), whether the desired outcome is successfully achieved can be accurately measured according to the present disclosure, whereas under the prior art systems, the success of this kind of treatment goal would not be accurately assessed.

Accordingly, an algorithm can detect the two closest points (P1 and P2) between the first tooth 330 and the second tooth 340 on the surfaces thereof. The two closest points (P1 and P2) can be respective points on each tooth with a minimum distance therebetween. That is, the two closest points (P1 and P2) have a distance therebetween that is less than a combination of any other two points (e.g., points P3 and P4) on the first tooth 330 and the second tooth 340.

An algorithm can detect points P1 and P2 automatically and assign the pair as dental references for the first tooth 330 and the second tooth 340 in the target virtual dental model. Such an algorithm can be used when a particular pair of adjacent virtual teeth on the target virtual dental model are spaced apart. As one of ordinary skill in the art will appreciate, spacing between adjacent teeth can be a component of an orthodontic treatment index score.

FIG. 4 illustrates an interproximation relationship between two overlapped virtual teeth according to one or more embodiments of the present disclosure. A first tooth 430 and a second tooth 440-1 in a target virtual dental model may be overlapped. In such a scenario, a single contact point does not exist between the first tooth 430 and the second tooth 440-1 because multiple contact points exist.

With respect to FIG. 4, the dotted outline of the second virtual tooth 440-1 indicates the position of the second tooth 440-1 in the treatment outcome virtual dental model. The solid outline of the second tooth 440-2 indicates a translation of the position of the second tooth as described herein.

An algorithm can compute such a translation to separate the first tooth 430 and the second tooth 440-2 by a very small space (e.g., 0.01 millimeters). Such a translation can be calculated as a translation that separates the first tooth 430 and the second tooth 440-2 by a minimum amount as compared to other translations.

Subsequent to the calculation and application of the translation, contact points (P1 and P2) for the first tooth 430 and the second tooth 440-2 can be calculated as described above with respect to FIG. 3. For calculating contact points, other methods may be used, including collision detection methods such as axis-aligned bounding boxes (AABB) tree and oriented bounding boxes (OBB) tree based collision detections. An OBB is a rectangular bounding box at an arbitrary orientation in 3D space. A collection of OBBs can be referred to as an OBB tree. An AABB is a rectangular bounding box constrained by edges parallel to coordinate axes. A collection of AABBs can be referred to as an AABB tree.

FIG. 5 illustrates an interproximation relationship between two point-contacted virtual teeth according to one or more embodiments of the present disclosure. A first tooth 530 and a second tooth 540 in a target virtual dental model may have a single point of contact. In such a scenario, the single contact point (P) can be used directly as a dental reference. The single contact point P can be assigned as one point, common to the first tooth 530 and the second tooth 540. The single contact point (P) can be assigned as two points (having the same coordinates if a common coordinate system is shared between the first tooth 530 and the second tooth 540), one on each tooth.

One or more embodiments of the present disclosure can employ other methods of assigning dental references to a target virtual dental model having one or more virtual teeth that are not in an "ideal" configuration. For example, typodont tooth morphing can be used to assign dental references to a target virtual dental model by morphing corresponding references from a virtual typodont (e.g., using a reference library of idealized tooth shapes).

As used herein a typodont refers to a virtual dental model including a number of ideal tooth shapes (e.g., from a reference library of idealized tooth shapes). Dental references (e.g., contact points) can be assigned to the typodont. Then, landmarks can be created on the typodont and corresponding landmarks can be created on the target virtual dental model. Additional discussion of a reference library of idealized tooth shapes can be found in U.S. patent application Ser. No. 11/888,742 entitled "Mapping Abnormal Dental References" filed Aug. 2, 2007, having at least one common inventor and assigned to Align Technology, Inc.

Such embodiments may be particularly useful for virtual teeth that have incomplete crows (e.g., representative of a chipped tooth, a partially erupted tooth, etc.). For example, a treatment professional may wish to use a cusp tip as a dental reference on a tooth that is chipped such that the tip is missing from the target virtual dental model. In such an example, the dental reference could be assigned to a typodont and then morphed from the typodont to the target virtual dental model to best approximate where the cusp tip should be located relative to the existing flat surface.

Based on the landmarks, a morphing function can be calculated for morphing from the typodont to the target virtual dental model. The morphing function can be applied to the dental references assigned to the typodont to obtain corresponding dental references on the target virtual dental model. Once dental references for the target virtual dental model have been obtained (e.g., assigned), an individualized orthodontic treatment index scoring system can operate as described herein.

In some embodiments, thin-plate spline based mapping can be used with respect to calculating a morphing function using the landmarks. Use of such a thin-plate spline may minimize the deformation energy effects (e.g., minimize the degree or extent of bend in the resulting surface between created landmarks). The deformation energy can be defined as:

$$\int\int_{R^2}\left(\frac{\partial^2 f}{\partial^2 x^2}\right)^2 + 2\left(\frac{\partial^2 f}{\partial x \partial y}\right)^2 + \left(\frac{\partial^2 f}{\partial^2 y^2}\right)^2 dxdy$$

Once the morphing function is calculated, it may be applied to the dental references assigned to the typodont to morph the same to the target virtual dental model. Additional discussion of typodont virtual models and morphing functions is described in U.S. patent application Ser. No. 11/951,812 entitled "System and Method for Improved Dental Geometry Representation" filed Dec. 6, 2007 having at least one common inventor with the present Application, and assigned to Align Technology, Inc.

One or more embodiments of the present disclosure can include mapping dental references from a target virtual dental model to a treatment outcome virtual dental model and/or an initial virtual dental model. Mapping dental reference points can include calculating a matching transform from the target virtual dental model (the entire model, and individual tooth therein, and/or one or more points therein) to the treatment outcome virtual dental model and/or initial virtual dental model. For example, an iterative closest point (ICP) algorithm can be used to calculate the matching transform.

An ICP algorithm can minimize the differences between two point clouds (e.g., between the target virtual dental model and the treatment outcome virtual dental model and/or the initial virtual dental model). The ICP algorithm can iteratively associate points between the two virtual dental models, estimate transformation parameters using a mean square cost function, and transform points from the first virtual dental model to the second virtual dental model using the estimated parameters. Such iteration can continue until the change in mean square error falls within a particular threshold. In some embodiments, a particular number of iterations can be selected rather than using a threshold limit in order to avoid slower processing times that may be associated with later iterations that converge on a local minimum.

Once the transform has been calculated it can be applied to a dental reference (e.g., a contact point) from the target virtual dental model to transform the dental reference to a corresponding dental reference on the treatment outcome virtual dental model and/or initial virtual dental model. The corresponding dental reference can be used as-calculated from the transform and/or the corresponding dental reference can be projected onto the surface of the treatment outcome virtual dental model and/or initial virtual dental model.

Examples of the calculation of transforms and projections for 3-D dental modeling applications are provided in U.S. patent application Ser. No. 12/583,479 entitled "Digital Dental Modeling" filed Aug. 21, 2009, having at least one common inventor with the present Application, and assigned to Align Technology, Inc.

Figure 6:
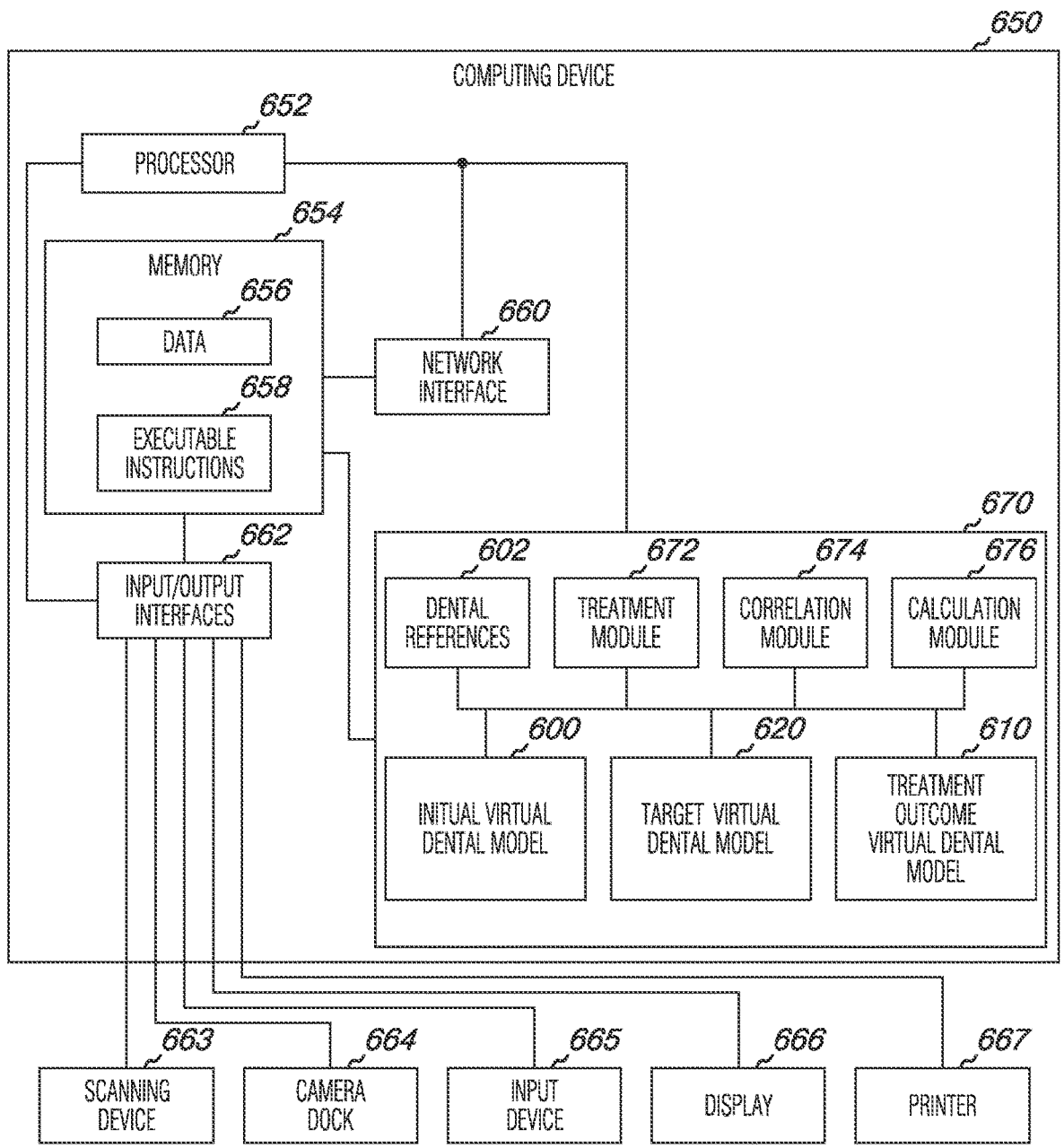
FIG. 6 illustrates a system for using an individualized orthodontic treatment index according to one or more embodiments of the present disclosure.

FIG. 6 illustrates a system for using an individualized orthodontic treatment index according to one or more embodiments of the present disclosure. In the system illustrated in FIG. 6, the system includes a computing device 650 having a number of components coupled thereto. The computing device 650 includes a processor 652 and memory 654. The memory can include various types of information including data 656 and executable instructions 658 as discussed herein.

Memory and/or the processor may be located on the computing device 650 or off the device in some embodiments. As such, as illustrated in the embodiment of FIG. 6, a system can include a network interface 660. Such an interface can allow for processing on another networked computing device or such devices can be used to obtain information about the patient or executable instructions for use with various embodiments provided herein.

As illustrated in the embodiment of FIG. 6, a system can include one or more input and/or output interfaces 662. Such interfaces can be used to connect the computing device with one or more input or output devices.

For example, in the embodiment illustrated in FIG. 6, the system can include connectivity to a scanning device 663, a camera dock 664, an input device 665 (e.g., a keyboard, mouse, etc.), a display device 666 (e.g., a monitor), a printer 667, and one or more other input devices 665. The input/output interface 662 can receive data, storable in the data storage device (e.g., memory 654), representing the digital dental model corresponding to the patient's upper jaw and the patient's lower jaw.

In some embodiments, the scanning device 663 can be configured to scan one or more physical molds of a patient's dentition. In one or more embodiments, the scanning device 663 can be configured to scan the patient's dentition directly. The scanning device 663 can be configured to input data to the application modules 670.

The camera dock 664 can receive an input from an imaging device (e.g., a two-dimensional imaging device) such as a digital camera or a printed photograph scanner. The input from the imaging device can be stored in the data storage device (e.g., memory 654).

The processor 652 can be configured to provide a visual indication of a virtual dental model on the display 666 (e.g., on a GUI running on the processor 652 and visible on the display 666). The GUI can be configured to allow a treatment professional to input treatment goals and/or to create a target virtual dental model 620. The GUI can be configured to allow a treatment professional to select and/or mark one or more dental references 602 on a virtual dental model (e.g., an initial virtual dental model 600, a target virtual dental model 620 and/or a treatment outcome virtual dental model 610). Input received via the GUI can be sent to the processor 652 as data and/or can be stored in memory 654.

Such connectivity can allow for the input and/or output of data and/or instructions among other types of information. Although some embodiments may be distributed among various computing devices within one or more networks, such systems as illustrated in FIG. 6 can be beneficial in allowing for the capture, calculation, and/or analysis of information discussed herein.

The processor 652, in association with the data storage device (e.g., memory 654), can be associated with data and/or application modules 670. The processor 652, in association with the memory 654, can store and/or utilize data and/or execute instructions to provide a number of application modules for using an individualized orthodontic treatment index.

Such data can include the initial virtual dental model 600, the target virtual dental model 620, and/or the treatment outcome virtual dental model 610. The initial virtual dental model 600 can be derived from a first scan of a patient's dentition and the treatment outcome virtual dental model 610 can be derived from a second (e.g., later) scan of the patient's dentition. The target virtual dental model 620 can include a number of dental references 602 assigned thereto.

Such application modules can include a treatment module 672, a correlation module 674, and/or a calculation module 676. The treatment module 672 can be configured to create the target virtual dental model 620 by modifying the initial virtual dental model 600 based on a treatment goal (e.g., a treatment goal specified by a treatment professional). The correlation module 674 can be configured to map a number of dental references 602 from the target virtual dental model 620 to the initial virtual dental model 600 and to the treatment outcome virtual dental model 610.

The calculation module 676 can be configured to calculate an individualized treatment index score for the treatment outcome virtual dental model 610 according to one or more differences between the target virtual dental model 620 and the treatment outcome virtual dental model 610 based on the number of dental references 602. For example, when the dental references 602 include contact points of anterior teeth, the calculation module 676 can be configured to calculate an alignment deviation of the patient's dentition based on the contact points of anterior teeth. When the dental references 602 include cusp tip points, the calculation module can be configured to calculate an arch length of the patient's dentition based on the cusp tip points.

When the dental references 602 include cuspid and molar widths, the calculation module can be configured to calculate an arch width of the patient's dentition based on the cuspid and the molar widths. When the dental references 602 include facial lines, the calculation module can be configured to calculate an arch curve of the patient's dentition based on the facial lines. When the dental references 602 include FACC lines, the calculation module can be configured to calculate an angulation and an inclination of the patient's dentition based on the FACC lines.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A system for orthodontic treatment planning, the system comprising:
one or more computing devices configured to evaluate implementation of an orthodontic treatment plan, wherein the one or more computing devices includes memory having executable instructions stored thereon that, when executed by one or more processors, cause the one or more computing devices to perform a method comprising:
generating a target dental model by modifying an initial dental model, wherein the initial dental model represents a patient's dentition at an initial stage of the orthodontic treatment plan, and the target dental model represents a target outcome for the patient's dentition;
graphically marking dental references on the target dental model based on a user's input to a graphical user interface, wherein graphically marking the dental references comprises assigning contact points between adjacent first and second teeth of the target dental model;
generating a treatment outcome dental model representing the patient's dentition after at least a portion of the orthodontic treatment has been completed, wherein the adjacent first and second teeth overlap in the treatment outcome dental model;
mapping the dental references marked on the target dental model to the treatment outcome dental model by:
calculating and applying a translation to minimally separate the first and second teeth from each other in the treatment outcome dental model; and
calculating contact points between the first and second teeth in the treatment outcome dental model using collision detection between the first and second teeth; and
calculating an individualized treatment index score for the treatment outcome dental model according to differences between the contact points of the target dental model and the contact points of the treatment outcome dental model.

2. The system of claim 1, wherein using detection collision comprises using bounding box calculations in three-dimensional (3D) space.

3. The system of claim 2, wherein the bounding box calculations are based on a collection of oriented bounding boxes (OBBs), where each OBB is a rectangular bounding box at an arbitrary orientation in 3D space.

4. The system of claim 1, wherein the individualized treatment index score is a first individualized treatment index score, the method further comprising:
mapping first locations of the dental references from the target dental model to third locations on the initial dental model;
comparing the first locations of the dental references of the target dental model and the third locations to identify second differences between the target dental model and the initial dental model; and
determining a second individualized treatment index score for the initial dental model using the second differences.

5. The system of claim 4, wherein the method further comprises:
comparing the first individualized treatment index score and the second individualized treatment index score; and
determining an improvement of the treatment outcome dental model relative to the target dental model, the improvement based on the comparison of the first individualized treatment index score and the second individualized treatment index score.

6. The system of claim 1, wherein calculating the individualized treatment index score comprises comparing the differences between the contact points of the target dental model and the contact points of the treatment outcome dental model by:
calculating a matching transform from at least a portion of the target dental model to at least a corresponding portion of the treatment outcome dental model; and
applying the matching transform to the dental references of the target dental model and the treatment outcome dental model.

7. The system of claim 6, wherein the method further comprises comparing first locations of the dental references of the target dental model and second locations of the treatment outcome dental model by projecting at least one dental reference from the at least the portion of the target dental model to the at least the corresponding portion of the treatment outcome dental model.

8. The system of claim 1, wherein the method further comprises receiving user input regarding treatment goals, wherein the target dental model is generated based on the user input regarding the treatment goals.

9. The system of claim 1, wherein graphically marking the dental references further comprises assigning one or more cusp tips on the target dental model, wherein the method further comprises calculating an arch length of the patient's dentition based on the one or more cusp tips.

10. The system of claim 1, wherein graphically marking the dental references further comprises assigning one or more facial lines on the target dental model, wherein the method further comprises calculating an arch curve of the patient's dentition based on the facial lines.

11. The system of claim 1, wherein graphically marking the dental references further comprises assigning one or more cuspid widths on the target dental model, wherein the method further comprises calculating an arch width of the patient's dentition based on the one or more cuspid widths.

12. The system of claim 1, wherein graphically marking the dental references further comprises assigning one or more molar widths on the target dental model, wherein the method further comprises calculating an arch width of the patient's dentition based on the one or more molar widths.

13. A non-transitory computing device readable medium having executable instructions executed by one or more processors to cause one or more computing devices to perform a method of digital orthodontic treatment planning using a graphical user interface, the method comprising:
generating a target dental model by modifying an initial dental model, wherein the initial dental model represents a patient's dentition at an initial stage of an orthodontic treatment plan, and the target dental model represents a target outcome for the patient's dentition;
graphically marking dental references on the target dental model based on a user's input to the graphical user interface, wherein graphically marking the dental references comprises assigning contact points between adjacent first and second teeth of the target dental model;

generating a treatment outcome dental model representing the patient's dentition after at least a portion of the orthodontic treatment plan has been completed, wherein the adjacent first and second teeth overlap in the treatment outcome dental model;

mapping the dental references marked on the target dental model to the treatment outcome dental model by:

calculating and applying a translation to minimally separate the first and second teeth from each other in the treatment outcome dental model; and calculating contact points between the first and second teeth in the treatment outcome dental model using collision detection between the first and second teeth; and calculating an individualized treatment index score for the treatment outcome dental model according to differences between the contact points of the target dental model and the contact points of the treatment outcome dental model.

14. The non-transitory computing device readable medium of claim 13, wherein using detection collision comprises using bounding box calculations in three-dimensional (3D) space.

15. The non-transitory computing device readable medium of claim 14, wherein the bounding box calculations are based on a collection of oriented bounding boxes (OBBs), where each OBB is a rectangular bounding box at an arbitrary orientation in 3D space.

16. The non-transitory computing device readable medium of claim 13, wherein the method further comprises receiving user input regarding treatment goals, wherein the target dental model is generated based on the user input regarding the treatment goals.

17. The non-transitory computing device readable medium of claim 13, wherein graphically marking the dental references further comprises assigning one or more cusp tips on the target dental model, wherein the method further comprises calculating an arch length of the patient's dentition based on the one or more cusp tips.

18. The non-transitory computing device readable medium of claim 13, wherein graphically marking the dental references further comprises assigning one or more facial lines on the target dental model, wherein the method further comprises calculating an arch curve of the patient's dentition based on the facial lines.

19. The non-transitory computing device readable medium of claim 13, wherein graphically marking the dental references further comprises assigning one or more cuspid widths on the target dental model, wherein the method further comprises calculating an arch width of the patient's dentition based on the one or more cuspid widths.

20. The non-transitory computing device readable medium of claim 13, wherein graphically marking the dental references further comprises assigning one or more molar widths on the target dental model, wherein the method further comprises calculating an arch width of the patient's dentition based on the one or more molar widths.

* * * * *